United States Patent [19]

Pálosi et al.

[11] Patent Number: 4,940,716
[45] Date of Patent: Jul. 10, 1990

[54] 2-AMINO-TETRAHYDRO-ISOQUINOLENE DERIVATIVES AND A PROCESS FOR THE PREPARATION THEREOF AND PHARMACEUTICAL COMPOSITIONS CONTAINING SAME

[75] Inventors: Endre Pálosi; Dezso Korbonits, both of Budapest; Erzsébet Molnár née Bako, Szodliger; Ida Szyoboda née Kanzel, Dunakeszi; László Harsing, Budapest; Gyorgy Simon, Budapest; Vera Gergely, Budapest; Peter Kormoczi, Budapest; Katalin Mármarosi née Keliner, Biatorbagy; Sandor Virág, Budapest, all of Hungary

[73] Assignee: Chinoin Gyogyszer es Vegyeszeti Termekek Gyara Rt, Budapest, Hungary

[21] Appl. No.: 295,920

[22] Filed: Dec. 29, 1988

[30] Foreign Application Priority Data

Dec. 30, 1987 [HU] Hungary ............................ 6132/87

[51] Int. Cl.$^5$ .................... C07D 217/00; A61K 31/47
[52] U.S. Cl. ..................................... 514/307; 546/143
[58] Field of Search ....................... 546/143; 514/307

[56] References Cited
U.S. PATENT DOCUMENTS
4,812,573 3/1989 Durant et al. ................... 514/307

Primary Examiner—Anton H. Sutto
Assistant Examiner—C. L. Cseh
Attorney, Agent, or Firm—Herbert Dubno; Jonathan Myers

[57] ABSTRACT

Diuretic and saluretic tetrahydro-isoquinoline derivatives of the Formula (I)

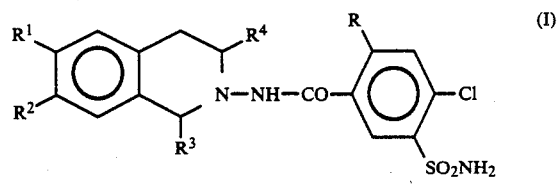

wherein
R stands for hydrogen or chlorine,
$R^1$ and $R^2$ are hydrogen, methoxy or ethoxy, and
$R^3$ and $R^4$ are hydrogen or methyl,
and a process for the preparation thereof as well as pharmaceutical compositions containing as active ingredients isoquinoline derivatives of the Formula (I). The compounds of Formula I are prepared by reacting a 2-amino-tetrahydro-isoquinoline derivative of the Formula (II)

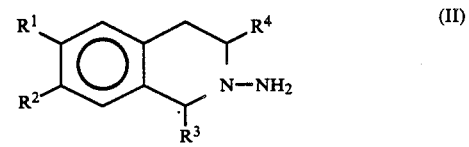

with a carboxylic acid derivative of the Formula (III)

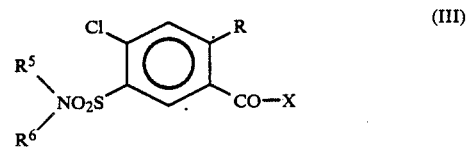

wherein
x stands for chlorine, —OH, —OCH$_2$CN, —OCH$_3$, —OC$_2$H$_5$, —OCOOCH$_3$ or —OCOOC$_2$H$_5$
$R^5$ and $R^6$ stand for hydrogen or together from CHN(CH$_3$)$_2$ and in case of the Formula (Ia)

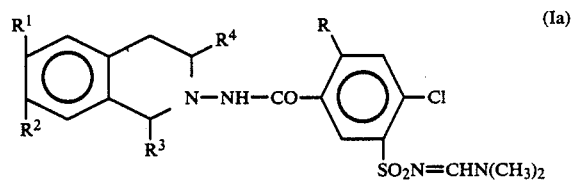

splitting off the protective group in alkaline medium.

6 Claims, No Drawings

2-AMINO-TETRAHYDRO-ISOQUINOLENE DERIVATIVES AND A PROCESS FOR THE PREPARATION THEREOF AND PHARMACEUTICAL COMPOSITIONS CONTAINING SAME

FIELD OF THE INVENTION

The present invention relates to tetrahydro-isoquinoline derivatives of the Formula (I)

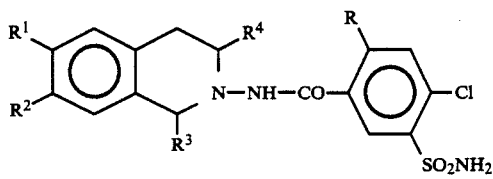

and a process for the preparation thereof as well as to pharmeceutical compositions containing as active ingredients isoquinoline derivatives of the Formula (I). The new compounds exhibit diuretic, hypertensive and saluretic activity.

In the Formula (I)
R stands for hydrogen or chlorine
$R^1$ and $R^2$ stand for hydrogen, methoxy or ethoxy
$R^3$ and $R^4$ stand for hydrogen or methyl.

BACKGROUND OF THE INVENTION

The chloro-benzene-sulfonamide type diuretic agents containing on the benzene ring a free carboxylic-group (Furosemid, DE PS No. 1,122,541 and K. Sturm, W. Siedel, R. Weyer, H. Ruschig: Chem. Ber. 99 328 (1966)), a carboxamide group (Diapamide, German Patent Publication No. 1,158,927 and L. T. Blouin, D. H. Kaump, R. L. Fransway, D. Williams: J. New Drugs 3, 302 (1963)) or a carboxylic acid hydrazide group (Clopamide, Hungarian Patent Specifications Nos. 150 352 and 152 300, A. Lindenmann, E. Schenker, E. Fluckinger, M. Taeschler: Arzneim.-Forsch. 13, 269 (1963)) are already known.

DESCRIPTION OF THE INVENTION

The chemical structure of the compounds of the invention is significantly different from that of the diuretic compounds of known structure mentioned above. Significant diuretic compounds containing an isoquinoline ring system have not been disclosed and therefore it is surprising that the compounds of the Formula (I) show a significant diuretic and saluretic activity. In a screening test carried out in rats (administered per os 5 mg/kg) the compounds according to the invention were compared with dihydrochlorothiazide and furosemid. Compounds prepared according to Examples 1 and 2 were particularly advantageous from the point of view of the secretion of urine amount and alkali metal ion and their Na/K ratio is also favorable.

It is particularly preferable that apart from their activity the therapeutic route of application of the compounds according to the invention is more advantageous than that of the "high ceiling" compounds as the diuretic and saluretic process is not so rapid and acute. After the administration the duration of the activity is 24 hours.

The acute toxicity of the compounds according to the invention is much lower than the toxicity of the comparative compounds and consequently the therapeutic index is also more favorable.

Tablets, coated tablets or capsules containing 1 to 300 mg active ingredient are used which contain the usual filling agents and carriers used for oral administration in human therapy.

The compounds of the Formula (I) wherein R, $R^1$, $R^2$, $R^3$ and $R^4$ are as given above, can be prepared according to the invention by reacting a 2-amino-tetrahydro-isoquinoline derivative of the Formula (II)

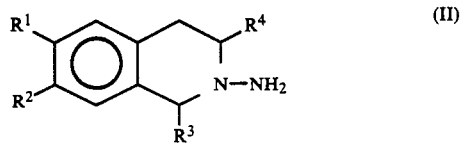

wherein $R^1$, $R^2$, $R^3$ and $R^4$ are as given above with a carboxylic acid derivative of the Formula (III)

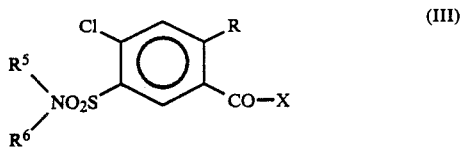

wherein
X stands for chlorine, —OH, —OCH$_2$CN, —OCH$_3$, —OC$_2$H$_5$, —OCOOCH$_3$ or —OCOOC$_2$H$_5$
R is as given above
$R^5$ and $R^6$ stand for hydrogen or together form CHN(CH$_3$)$_2$ and in case of the Formula (Ia)

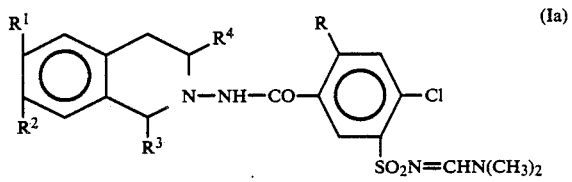

wherein R, $R^1$, $R^2$, $R^3$ and $R^4$ are as given above. The protective group is split off in alkaline medium according to reaction scheme A.

Reaction Scheme "A"

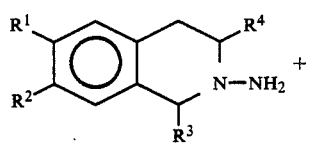

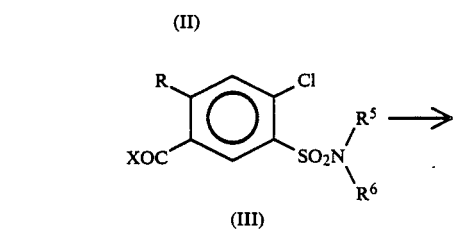

-continued

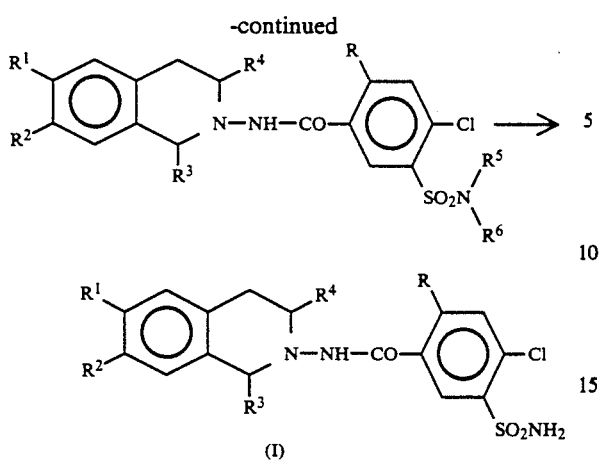

In this reaction a free carboxylic acid or a reactive derivative thereof, such as acid halide, lower alkyl or active ester thereof or a mixed anhydride is used for acylation. As an alkyl ester preferably methyl or ethyl ester and as active ester a cyano-methyl ester can be used. The reactants are used in an equimolar amount and triethyl amine or sodium amide is added to the reaction mixture.

In certain cases it may be preferred to substitute the sulfonamide group. For this purpose condensation with formamide-acetals can be used where amino-methylidene-sulfamides are formed according to reaction scheme B.

Reaction Scheme "B"

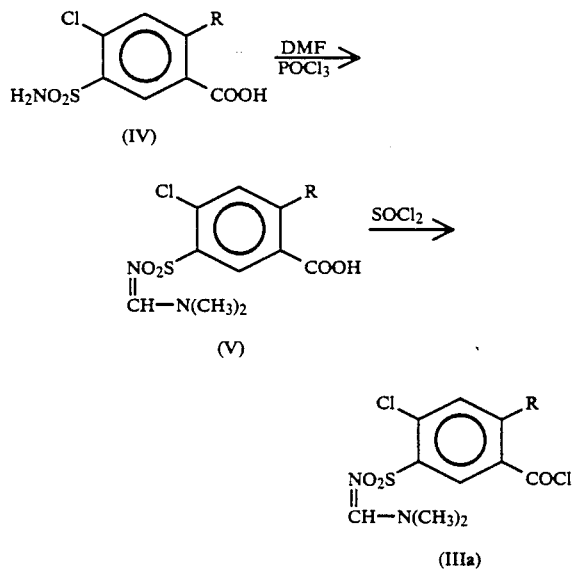

This reaction is particularly important if acid chlorides are used for the acylation according to reaction scheme A. These "protected" acid chlorides are much more stable compounds than the corresponding compounds containing a free sulfonamide. The reaction may be performed in dimethylformamide at a temperature ranging from 40° to 80° C. and using dimethyl formamide-dimethyl acetal.

The preparation of the compounds of the Formula (V)

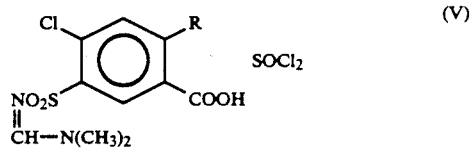

can preferably be performed by preparing dimethyl formamide-dimethyl acetal in situ in the reaction mixture and by reacting this sulfonamide group immediately with the "protected" acid of the Formula (V) and the formed compound is reacted with thionyl-chloride and thus the acid chloride of the Formula (IIIa)

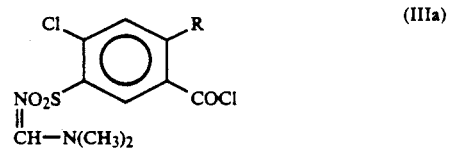

is obtained with a good yield.

The acylation with acid chlorides or mixed anhydrides may be carried out in polar solvents, such as tetrahydrofuran, dioxane, pyridine, dimethyl formamide, dimethyl acetamide, dimethyl urea. In the course of the reaction the temperature may be in the range from −20° C. to the boiling point of the solvent. If a non-basic solvent, such as pyridine, is used then as an acid binding agent organic bases, such as triethyl amine, dimethyl aniline, can be used.

The acid chlorides of the Formula (III) (wherein X stands for chlorine) may be used for acylation and one may proceed by carrying out the acylation in a mixture of water and a water miscible organic solvent and in the presence of an alkali or alkali earth metal carbonate or a hydrogen carbonate as an acid binding agent.

As water miscible organic solvents protic or aprotic solvents can be used. As an aprotic solvent ether type solvents, such as dioxane, tetrahydrofuran, or ketone type solvents, such as acetone, or acid amides, such as dimethyl formamide, dimethyl acetamide may be used. As a protic solvent lower aliphatic alcohols, such as methyl, ethyl or propyl alcohol are preferred.

As an alkali metal carbonate sodium carbonate or potassium carbonate and as an alkaline earth metal carbonate magnesium and calcium carbonate and as an alkali metal hydrogen carbonate sodium and potassium hydrogen carbonate can be used. The reaction may preferably be performed at a temperature from 0° to 100° C., particularly preferably at 10° to 30° C.

In order to prepare the mixed anhydride an acid of the Formula (V) can be reacted with an alkyl ester of chloro-carbonic acid. Preferably the methyl or ethyl ester of chloro-carbonic acid is applied. The mixed anhydride may be separated or preferably prepared in the reaction mixture and reacted further without isolation with an amino compound of the Formula (II).

The removal of the protecting group may be carried out by alkaline hydrolysis. The reaction may be performed in an aqueous medium by using strong inorganic bases, preferably sodium or potassium hydroxide. The used temperature is between 20° to 80° C., preferably 50° to 60° C. For 1 mole of compound to be hydrolyzed, 2 to 6, preferably 3 to 4, moles of inorganic base is used.

If as a carboxylic acid a compound is used where in the general Formula (III) X stands for hydroxyl and R, $R^5$ and $R^6$ are as given above, as an acylating agent then the reaction is carried out in the presence of a condensing agent. For this purpose dicyclohexyl-carbodiimide or tetrachloro-silane can be used. The reaction is preferably performed in pyridine.

In rat experiments one can determine the excellent saluretic activity of the compounds of the invention, the activity can be observed 1 to 2 hours after administration. The maximal activity is achieved 3 to 5 hours and it lasts for 24 hours ensuring thereby a protecting and longlasting diuresis. A particular advantage of the new compounds is the favorable sodium-potassium ratio and the low toxicity. $LD_{50}$ for mice for per os administration is higher than 3,000 mg/kg.

1 to 300 mg active ingredient are used for oral administration in human therapy and tablets, coated tablets and capsules containing the usual filling agents and carriers are used.

Specific Examples

The details of the invention can be found in the following non-limiting examples.

EXAMPLE 1

43.2 g of 2-amino-1,2,3,4-tetrahydro-isoquinoline-hydrochloride (it is prepared according to J. Het. Chem. 20, 121 (1983)) and 24.5 g of calcium-carbonate are stirred for 30 minutes in a 2:1 mixture of 400 cm$^3$ dioxane and water. In small portions under stirring 59.5 g 4-chloro-3-sulfamoyl-benzoylchloride are added to the suspension at room temperature (its preparation is disclosed in J. Med. Chem. 11, 970 (1968)). The reaction mixture is stirred for 2 hours and diluted with 300 cm$^3$ water. The separating crystals are sucked down and washed with water with 0.5N hydrochloric acid and then again with water. 71.9 g (84%) 2-[(3'-sulfamoyl-4'-chloro)-benzoyl]-amino-1,2,3,4-tetrahydro-isoquinoline are obtained in the form of white crystals. After recrystallization the product melts at 225°–228° C.

Analysis for the Formula $C_{16}H_{16}ClN_3O_3S$: Calculated: C: 52.53%; H: 4.41%; N: 11.49%; Cl: 9.69%; S: 8.77%; Found: C: 52.26%; H: 4.41%; N: 11.32%; Cl: 9.86%; S: 8.90.

EXAMPLE 2

One may proceed according to Example 1 and as starting material 28.2 g of 1-methyl-2-amino-1,2,3,4-tetrahydro-isoquinoline, 17.5 g of calcium-carhonate, 43.2 g of 4-chloro-3-sulfamoyl-benzoyl-chloride and a 2:1 mixture of 350 cm$^3$ dioxane and water are used. 48.3 g (74.8%) 1-methyl-2-[(3'-sulfamoyl-4'-chloro)-benzoyl]-amino-1,2,3,4-tetrahydro-isoquinoline are obtained. After precipitation the obtained product melts at 227°–229° C.

Analysis for the Formula $C_{17}H_{18}ClN_3O_3S$: Calculated: C: 53.75%; H: 4.78%; N: 11.06%; Cl: 9.33%; S: 8.44%; Found: C: 53.86%; H: 4.66%; N: 11.17%; Cl: 9.41%; S: 8.48.

The preparation of the starting materials (A) 21.5 g of 1-methyl-1,2,3,4-tetrahydro-isoquinolinehydrochloride (its preparation: Monatshefte, volume 53–54, 959 (1929) are dissolved in 50 cm$^3$ water and to the solution a solution of 8.22 g of sodium nitrite in 25 cm$^3$ water is added within 1 hour at 75° C. dropwise. The reaction mixture is cooled at 75° C. after stirring for 2 hours and it is extracted with 6×30 cm$^3$ chloroform. The chloroform solution is washed with 50 cm$^3$ water, dried and evaporated in vacuo. 19.2 g (93%) 1-methyl-2-nitroso-1,2,3,4-tetrahydro-isoquinoline are obtained as a brown oil which is used for the next step without further purification.

(B) The nitroso compound obtained in the previous step is dissolved in 32 cm$^3$ glacial acetic acid and the solution is added dropwise under cooling with ice-water under stirring to a suspension of 31.9 g zinc powder in 30 cm$^3$ water. The reaction mixture is cooled to 1 hour with icy water and stirred without cooling for 2 hours. The mixture is heated to 85° C., it is filtered and the residual zinc is washed with 3×20 cm$^3$ 5% aqueous hot hydrochloric acid. The filtrate is alkalized with a 40% sodium-hydroxide solution and extracted with 4×100 cm$^3$ chloroform. The chloroform solution is washed with water, dried and evaporated in vacuo. 18 g (100%) of 1-methyl-2-amino-1,2,3,4-tetrahydro-isoquinoline is obtained as a brown oil which can be used without further purification.

EXAMPLE 3

The process according to Example 2 is used and as starting material 28.1 g 1-methyl-2-amino-6,7-dimethoxy-1,2,3,4-tetrahydro-isoquinoline (its preparation is disclosed in J. prakt. Chem. 327, 445 (1985)), 7 g calcium-carbonate, 32.1 g 4-chloro-3-sulfamoyl-benzoyl-chloride and 20 cm$^3$ of a 2:1 mixture of dioxane and water are used. 50 g (90%) of a 1-methyl-2-[(3'-sulfamoyl-4'-chloro-benzoyl)-amino]-6,7-dimethoxy-1,2,3,4-tetrahydro-isoquinoline-monohydrate are obtained; melting point 230°–233° C.

Analysis for the Formula $C_{19}H_{22}ClN_3O_5S \cdot xH_2O$: Calculated: C: 49.83%; H: 5.28%; N: 9.18%; Cl: 7.74%; S: 7.00%; Found: C: 49.58%; H: 5.00%; N: 8.84%; Cl: 7.50%; S: 6.81.

EXAMPLE 4

The process of Example 1 is used but the reaction is carried out in a 2:1 mixture of 400 cm$^3$ isopropyl-alcohol and water 70.1 g (82%) 2-[(3'-sulfamoyl-4'-chloro-benzoyl)-amino]-1,2,3,4-tetrahydro-isoquinoline are obtained. After recrystallization the product melts at 226°–228° C.

EXAMPLE 5

22.6 g of 2-amino-1,2,3,4-tetrahydro-isoquinoline are dissolved in 400 cm$^3$ dioxane and to the solution a solution of 12.7 g of anhydrous sodium-carbonate in 200 cm$^3$ water is added. The mixture is cooled with cold water and stirred and a solution of 68 g 4-chloro-3-[(N-dimethyl-amino-methylidene)-sulfamoyl-benzoyl]-chloride in 400 cm$^3$ dioxane is added dropwise while the temperature is maintained at 15° to 20° C. When the addition is completed the reaction mixture is stirred for 2 hours at 20° C. and it is filtered in order to get a clear solution. The filtrate is diluted with 2 l water and the separated crystals are sucked down, washed with water and dried at 80° C. The crude product (63 g) is stirred for 8 hours at 50° C. with 430 cm$^3$ 2N sodium hydroxide solution. The solution is activated with charcoal, filtered and the pH of the filtrate is adjusted to 6 by adding 2N hydrochloride acid under cooling and stirring.

The precipitated product is sucked down, washed with water and dried at 80° C. 43.9 g (60%) of 2-[(3'-sulfamoyl-4'-chloro)-benzoyl]-amino-1,2,3,4-tetrahydro-isoquinoline are obtained melting at 225°–227° C.

The preparation of the starting materials:

14.5 g 4-chloro-3-[(N-dimethylamino-methylidene)-sulfamoyl]-benzoic acid (see Dutch Patent Specification No. 7,604,356) are suspended in 50 cm³ thionyl-chloride and to the suspension 2 drops of dimethyl-formamide are added and the reaction mixture is boiled under stirring for 2 hours. The mixture is filtered to get a clear solution and the filtrate is evaporated in vacuo. 12.7 g (82%) of 4-chloro-3-[(N-dimethyl-amino-methylidene)-sulfamoyl]-benzoyl-chloride are obtained in the form of white crystals melting at 140° C. After recrystallization from benzene the melting point is 154°–155° C.

Analysis for the Formula $C_{10}H_{10}Cl_2N_2O_3S$: Calculated: C: 38.84%; H: 3.26%; N: 9.06%; Cl: 22.93%; S: 10.37%; Found: C: 38.28%; H: 3.07%; N: 8.94%; Cl: 23.14%; S: 10.58.

EXAMPLE 6

8.27 g of 2-amino-1,2,3,4-tetrahydro-isoquinoline are suspended in 25 cm³ pyridine and to the suspension 17.25 g of 4-chloro-3-[(N-dimethylamino-methylidene)-sulfamoyl]-benzoyl-chloride are added and the reaction mixture is heated at 60°–70° C. and a yellow solution is obtained. The thick yellow solution is allowed to stand overnight and the next day 200 cm³ of water are added. A yellow gum is separated which is disintegrated after stirring for a few minutes into a beige powder. The product is sucked down, washed with water and dried. 21 g of crude product is hydrolyzed as disclosed in Example 5 with 143 cm³ of a 2N sodium hydroxide solution. 15.4 g (75%) 2-[(3'-sulfamoyl-4-chloro-benzoyl)-amino]-1,2,3,4-tetrahydro-isoquinoline are obtained melting at 225°–227° C.

EXAMPLE 7

We may proceed as disclosed in Example 4 with the exception that the reaction is carried out in 350 cm³ of a 2:1 mixture of ethanol and water.

The test of salidiuretic compounds in rats

Screen tests were carried out in masculine rats belonging to LATI CFY strain weighing at an average 240 g. The animals obtained standard rat nourishment. 16 hours before the experiment the animals were deprived of nourishment but the liquid uptake was not restricted. In order to show diuretic activity the procedure of Lipschitznek modified by Kagawa and Kalm was used. (Arch. Int. Pharmacodyn. 137, 241–249 (1962). The animals were placed into a metabolism cage. The urine collection was carried out in 0–6 and 0–24 hour periods. The control animals were administered 25 cm³/kg physiological salt solution through a gastric tube. The test substance was administered to the animals through a gastric tube at a dose of 5 mg/kg in physiological salt solution of an amount corresponding to the amount of physiological salt solution given to the control animals. After 6 hours the animals were administered the same volume of physiological saline solution as the volume excreted with 0–6 hours through a gastric tube.

The amount of secreted urine between 0 to 6 and 0 to 24 hours was measured and calculated together with the concentration of sodium and potassium and the Na/K ratio of the urine secreted within a given period.

Simultaneously with each test control groups treated with physiological salt solution and hypothiazide were used.

Effect of a single oral dose of 5 mg/kg of the compouns on the secretion of water, sodium and potassium within 0–6 and 0–24 hours in the % of the simultaneously measured control values and on the secreted Na/K.

| According to Example No. | Water | | Na | | K | | Na/K | |
|---|---|---|---|---|---|---|---|---|
| | 0–6 h | 0–24 h | 0–6 h | 0–24 h | 0–6 h | 0–24 h | 0–6 h | 0–24 h |
| Control | 100 | 100 | 100 | 100 | 100 | 100 | 1.81 | 2.45 |
| 1. | 216 | 148 | 260 | 152 | 145 | 82 | 9.09 | 5.94 |
| 2. | 233 | 154 | 279 | 151 | 170 | 100 | 7.56 | 5.38 |
| 3. | 147 | 112 | 186 | 121 | 104 | 84 | 4.74 | 3.99 |
| Hypothiazide | 159 | 119 | 187 | 123 | 117 | 109 | 3.90 | 3.50 |

We claim:

1. A compound of the Formula (I)

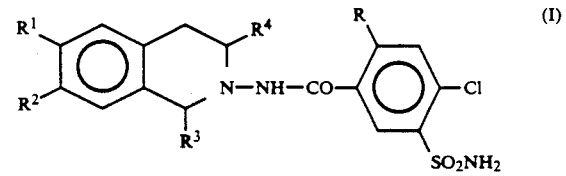

wherein

R is hydrogen or chlorine $R^1$ and $R^2$ are hydrogen, methoxy or ethoxy, and $R^3$ and $R^4$ are hydrogen or methyl.

2. A diuretic and saluretic method of treatment which comprises administering to a subject requiring diuretic or saluretic treatment in a dosage form in an effective amount.

3. A compound of the Formula (Ia)

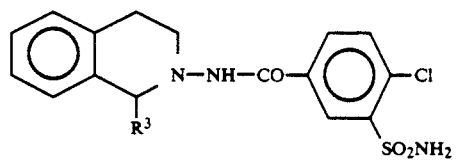

wherein $R^3$ is hydrogen or methyl.

4. 2-[(3'-sulfamoyl-4'-chloro)-benzoyl]-amino-1,2,3,4-tetrahydro-isoquinoline as defined in claim 3.

5. 1-methyl-2-[(3'-sulfamoyl-4'-chloro)-benzoyl]-amino-1,2,3,4-tetrahydro-isoquinoline as defined in claim 3.

6. A diuretic and saluretic pharmaceutical composition which comprises a therapeutically effective amount of the compound of the Formula (I) as defined in claim 1 together with a pharmaceutically acceptable inert carrier.

* * * * *

UNITED STATES PATENT AND TRADEMARK OFFICE
CERTIFICATE OF CORRECTION

PATENT NO. : 4 940 716
DATED : 10 July 1990
INVENTOR(S) : Endre PALUSI et al.

It is certified that error appears in the above-identified patent and that said Letters Patent is hereby corrected as shown below:

Claim 2, line 2 as it appears in
col. 8, lines 36 to 39,
for "administering" read:
-- administering a compound as defined in claim 1 -- .

Signed and Sealed this

Second Day of March, 1993

Attest:

STEPHEN G. KUNIN

Attesting Officer

Acting Commissioner of Patents and Trademarks